(12) United States Patent
Mitra et al.

(10) Patent No.: US 9,937,225 B2
(45) Date of Patent: *Apr. 10, 2018

(54) TOPICAL FORMULATIONS AND USES THEREOF

(71) Applicant: OCULAR TECHNOLOGIES SARL, Epalinges (CH)

(72) Inventors: Ashim K. Mitra, Overland Park, KS (US); Sidney L. Weiss, Randolph, NJ (US)

(73) Assignee: SUN PHARMA GLOBAL FZE, Sharjah (AE)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,510

(22) Filed: May 12, 2016

(65) Prior Publication Data

US 2016/0256520 A1  Sep. 8, 2016

Related U.S. Application Data

(63) Continuation of application No. 14/611,993, filed on Feb. 2, 2015, which is a continuation-in-part of application No. 13/975,175, filed on Aug. 23, 2013, now Pat. No. 8,980,839.

(60) Provisional application No. 61/693,189, filed on Aug. 24, 2012.

(51) Int. Cl.

| A61K 38/13 | (2006.01) |
| A61K 47/44 | (2017.01) |
| A61K 9/00 | (2006.01) |
| A61K 47/10 | (2017.01) |
| A61K 9/107 | (2006.01) |
| A61K 31/202 | (2006.01) |

(52) U.S. Cl.
CPC ............ *A61K 38/13* (2013.01); *A61K 9/0048* (2013.01); *A61K 9/1075* (2013.01); *A61K 31/202* (2013.01); *A61K 47/10* (2013.01); *A61K 47/44* (2013.01)

(58) Field of Classification Search
CPC .... A61K 38/13; A61K 9/0048; A61K 9/1075; A61K 31/202; A61K 47/10; A61K 47/44
See application file for complete search history.

(56) References Cited

U.S. PATENT DOCUMENTS

| 5,484,597 | A | 1/1996 | Slavtcheff et al. |
| 5,843,891 | A | 12/1998 | Sherman |
| 5,951,971 | A | 9/1999 | Kawashima et al. |
| 5,998,365 | A | 12/1999 | Sherman |
| 6,071,958 | A | 6/2000 | Jimenez-Bayardo |
| 7,087,237 | B2 | 8/2006 | Peyman |
| 8,435,544 | B2 | 5/2013 | Mitra et al. |
| 8,535,694 | B2 | 9/2013 | Mitra et al. |
| 8,980,839 | B2 | 3/2015 | Mitra et al. |
| 9,017,725 | B2 | 4/2015 | Mitra et al. |
| 2005/0042198 | A1 | 2/2005 | Smith et al. |
| 2006/0205639 | A1 | 9/2006 | Domb et al. |
| 2007/0248645 | A1 | 10/2007 | Bague et al. |
| 2007/0249632 | A1 | 10/2007 | Zentner et al. |
| 2008/0299206 | A1 | 12/2008 | Lee et al. |
| 2009/0092665 | A1 | 4/2009 | Mitra et al. |
| 2009/0209599 | A1 | 8/2009 | Endo et al. |
| 2009/0234004 | A1 | 9/2009 | Kabra et al. |
| 2009/0286718 | A1 | 11/2009 | Stringer |
| 2009/0298956 | A1 | 12/2009 | Chowhan et al. |
| 2010/0310462 | A1 | 12/2010 | Sberg et al. |
| 2010/0310642 | A1 | 12/2010 | Mitra et al. |
| 2011/0021443 | A1 | 1/2011 | Lambert et al. |
| 2011/0040113 | A1 | 2/2011 | Wu et al. |
| 2011/0152264 | A1 | 6/2011 | Reunamaki et al. |
| 2011/0300195 | A1 | 12/2011 | Mitra et al. |
| 2011/0311592 | A1 | 12/2011 | Birbara et al. |
| 2013/0045927 | A1 | 2/2013 | Dana et al. |
| 2014/0057854 | A1 | 2/2014 | Mitra et al. |
| 2015/0148299 | A1 | 5/2015 | Mitra et al. |
| 2015/0165048 | A1 | 6/2015 | Mitra et al. |

FOREIGN PATENT DOCUMENTS

| EP | 2478906 | 7/2012 |
| EP | 2887923 | 7/2015 |
| JP | 2004-238346 | 8/2004 |
| WO | 2004096261 | 11/2004 |
| WO | 2009048929 | 4/2009 |
| WO | 2014032026 | 2/2014 |

OTHER PUBLICATIONS

Definition of "lipids" from the IUPAC Compendium of Chemical Terminology (Gold Book) downloaded on Jun. 2, 2017 from http://goldbook.iupac.org/src_PAC1995671307.html.*
"Vitamin E" from Medline Plus downloaded on Jun. 2, 2017 from https://medlineplus.gov/ency/article/002406.htm.*
"Cremophor RH 40", Technical Information, BASF, Oct. 2010.
U.S. Appl. No. 13/975,175, "Final Office Action", dated Apr. 1, 2014, 18 Pages.
U.S. Appl. No. 13/975,175, "Non-Final Office Action", dated Dec. 19, 2013, 10 pages.
U.S. Appl. No. 13/975,175, "Non-Final Office Action", dated Jul. 22, 2014, 17 pages.
U.S. Appl. No. 13/975,175, "Notice of Allowance", dated Jan. 2, 2015, 7 pages.

(Continued)

*Primary Examiner* — Christina Bradley
(74) *Attorney, Agent, or Firm* — Medler Ferro Woodhouse & Mills

(57) ABSTRACT

Provided herein include formulations for topical administration, such as ophthalmic formulations, and methods of using such formulations. In some aspects and embodiments the formulations may include a polyoxyl lipid or fatty acid, and or a polyalkoxylated alcohol and may include nanomicelles. Also include methods of treating or preventing diseases or conditions, such as ocular diseases or conditions.

17 Claims, No Drawings

(56) References Cited

OTHER PUBLICATIONS

U.S. Appl. No. 14/611,993, "Non-Final Office Action", dated Nov. 10, 2015, 15 pages.
U.S. Appl. No. 14/611,993, "Non-Final Office Action", dated Nov. 18, 2015, 16 pages.
U.S. Appl. No. 14/629,883, "Non-Final Office Action", dated Nov. 13, 2015, 22 pages.
Donnenfeld et al., "Topical Ophthalmic Cyclosporine: Pharmacology and Clinical Uses", Survey of Ophthalmology, vol. 54, No. 3, 2009, pp. 321-338.
EP13831463.8 , "Extended European Search Report", dated Feb. 26, 2016, 8 pages.
Na et al., "Resolvin E1 Improves Tear Production and Decreases Inflammation in a Dry Eye Mouse Model", Journal of Ocular Pharmacology and Therapeutics, vol. 26, No. 5, Oct. 2010, pp. 431-439.
Schmidts et al., "Influence of hydrophilic surfactants on the properties of multiple W/O/W emulsions", Journal of Colloid and Interface Science, vol. 338, No. 1, 2009, pp. 184-192.
International Search Report dated Nov. 18, 2013, in International Application No. PCT/US2013/056513.
J.D. Quintana-Hau et al., "Characterization of the Novel Ophthalmic Drug Carrier Sophisen in Two of Its Derivatives: 3A Ofteno™ and Modusik-A Ofteno™," Drug Development and Industrial Pharmacy, 2005, vol. 31, pp. 263-269.
Restasis Prescribing Information, Allergan, Inc., downloaded Mar. 23, 2014.
PCT/US2016/029602, "International Search Report and Written Opinion", dated Jul. 15, 2016, 11 pages.
PCT/US2016/060391, "International Search Report and Written Opinion", dated Jan. 10, 2017, 9 pages.

\* cited by examiner

TOPICAL FORMULATIONS AND USES THEREOF

CLAIM OF PRIORITY

This application is a continuation of U.S. application Ser. No. 14/611,993, filed Feb. 2, 2015, which is a continuation of U.S. application Ser. No. 13/975,175, filed on Aug. 23, 2013, which claims priority to U.S. Provisional Application No. 61/693,189, filed on Aug. 24, 2012, each of which are hereby incorporated by reference in their entirety.

FIELD OF THE INVENTION

The present disclosure relates to the field of formulations for topical administration, such as ophthalmic formulations, and methods of using such formulations.

BACKGROUND OF THE INVENTION

The information provided herein and references cited are provided solely to assist the understanding of the reader, and does not constitute an admission that any of the references or information is prior art to the present invention.

United States Patent Application Nos US2010/0310462 and US2009/0092665 disclose drug delivery systems for ophthalmic use that have nanomicelles that include vitamin E TPGS.

Travoprost involves a formulation for glaucoma or ocular hypertension that includes HCO-40 and a prostaglandin analog as the active ingredient. See dailymed.nlm.nih.gov/dailymed/lookup.cfm?setid=338e7ff4-0d91-4208-a45d-bfa2be52334d on the world-wide web. The active ingredient is present at 0.004%. The formulation includes propylene glycol and does not include nanomicelles. HCO-40 is present in Travoprost at 0.5%. See ema.europa.eu/docs/en_GB/document_library/EPAR_-_Product_information/human/000665/WC500038389.pdf on the world-wide web.

SUMMARY OF THE INVENTION

The present disclosure relates to topical formulations such as formulations suitable for ophthalmic administration of an active ingredient. In certain aspects and embodiments, the formulations of the present disclosure may include a polyoxyl lipid or fatty acid, and or a polyalkoxylated alcohol and may include nanomicelles.

In certain aspects and embodiments as described herein, the formulations as described herein may have certain surprising features and advantages that could not have been predicted prior to the present disclosure. For example, formulations of the instant disclosure may be able to support a dose of an active ingredient such as a hydrophobic active ingredient that is surprisingly higher than many prior art formulations. The dose of an active ingredient or agent used in the formulations described herein may be selected based on various criteria, including the amount that the formulation can support, the desired dose for various therapeutic applications, etc. In this regard, in some embodiments the active ingredient (such as for ophthalmic administration) the active agent may be at least about 0.05%, or at least about 0.08%, or at least about 0.09%, or at least about 0.1%, or at least about 0.15%; or at least about 0.2%: or at least about 0.3%: or at least about 0.4%; or at least about 0.5%; or at least about 0.6%; or at least about 0.7%; or at least about 0.8%; or at least about 0.9%; or at least about 1.0%; or at least about 1.5%; or at least about 2%; or at least about 3%; or at least about 4%; or at least about 5%; or between 0.05 and 5%; or between 0.05 and 0.5%; or between 0.05 and 0.2%, or between 0.08 and 0.12%; or between 0.1 and 0.5%, or between 0.5 and 1%, or between 0.5 and 1.5%; or between 1 and 5%; or between 2 and 4%; or between 4 and 6% of the formulation. In some embodiments the formulation has nanomicelles with a relatively increased entrapment efficiency; in such embodiments the active agent (such hydrophobic active agents for ophthalmic administration) may be at least about 0.05%, or at least about 0.08%, or at least about 0.09%, or at least about 0.1%, or at least about 0.15%; or at least about 0.2%: or at least about 0.3%: or at least about 0.4%; or at least about 0.5%; or at least about 0.6%; or at least about 0.7%; or at least about 0.8%; or at least about 0.9%; or at least about 1.0%; or at least about 1.5%; or at least about 2%; or at least about 3%; or at least about 4%; or at least about 5%; or between 0.05 and 5%; or between 0.05 and 0.5%; or between 0.05 and 0.2%, or between 0.08 and 0.12%; or between 0.1 and 0.5%, or between 0.5 and 1%, or between 0.5 and 1.5%; or between 1 and 5%; or between 2 and 4%; or between 4 and 6% of the formulation and is present in nanomicelles of the formulation. In certain aspects and embodiments, the formulations of the disclosure are surprisingly effective in dissolving and/or delivering active ingredients (such as hydrophobic active ingredients) without a need for organic solvents (such as propylene glycol) that can be an irritant when included in ophthalmic formulations. In some embodiments, the formulations of the present disclosure are surprisingly stable at high temperatures, for example, temperatures above about 40 degrees C. In some aspects and embodiments the nanomicellular nature of some formulations described herein allow for improved ocular tissue distribution. In certain aspects and embodiments, formulations as described herein are particularly suitable for anterior eye delivery, or posterior eye delivery, or anterior and posterior eye delivery. Moreover, the formulations of certain aspects and embodiments of the disclosure may have the surprising advantage of being adaptable to facilitate delivery of active agents having various sizes or properties; for example, in certain embodiments in formulations that include a polyoxyl castor oil, HCO-60 could be used for active agents having relatively small molecule sizes and HCO-80 and/or HCO-100 could be used for relatively larger sized active agents.

Accordingly, in a first aspect provided is an ophthalmic formulation that includes an active agent, a polyoxyl lipid or fatty acid and a polyalkoxylated alcohol. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-60. In some embodiments the polyoxyl lipid is HCO-80. In some embodiments the polyoxyl lipid is HCO-100. In some embodiments, the formulation includes a polyalkoxylated alcohol that is octoxynol-40. In some embodiments, the formulation includes a polyalkoxylated alcohol (such as octoxynol-40) present between 0.002 and 4%; or between 0.005 and 3%; or 0.005 and 2%; or 0.005 and 1%; or 0.005 and 0.5%; or 0.005 and 0.1%; or 0.005 and 0.05%; or 0.008 and 0.02%; or about 0.01% by weight of the formulation.

As used herein, the term "polyoxyl lipid or fatty acid" refers to mono- and diesters of lipids or fatty acids and polyoxyethylene diols. Polyoxyl lipids or fatty acids may be numbered ("n") according to the average polymer length of the oxyethylene units (e.g., 40, 60, 80, 100) as is well understood in the art. The term "n≥40 polyoxyl lipid" means that the ployoxyl lipid or fatty acid has an average oxyethylene polymer length equal to or greater than 40 units. Stearate hydrogenated castor oil and castor oil are common lipids/fatty acids commercially available as polyoxyl lipids or fatty acid, however, it is understood that any lipid or fatty acid could polyoxylated to become a polyoxyl lipid or fatty acid as contemplated herein. Examples of polyoxyl lipid or fatty acids include without limitation HCO-40, HCO-60, HCO-80, HCO-100, polyoxyl 40 stearate, polyoxyl 35 castor oil.

In some embodiments of any of the compositions and methods described herein, the average polymer length of the oxyethylene units of a polyoxyl lipid or fatty acid is longer for a relatively larger active ingredient and is shorter for a relatively smaller active ingredient; for example in some embodiments in which the active ingredient is a resolvin or resolvin-like compound the polyoxyl lipid is HCO-60 and in some embodiments where the active ingredient is cyclosporine A (which is larger than a resolvin) the polyoxyl lipid is HCO-80 or HCO-100.

As used herein, the term "micelle" or "nanomicelle" refers to an aggregate (or cluster) of surfactant molecules. Micelles only form when the concentration of surfactant is greater than the critical micelle concentration (CMC). Surfactants are chemicals that are amphipathic, which means that they contain both hydrophobic and hydrophilic groups. Micelles can exist in different shapes, including spherical, cylindrical, and discoidal. A micelle comprising at least two different molecular species is a mixed micelle. The in some embodiments, ophthalmic compositions of the present disclosure include an aqueous, clear, mixed micellar solution In a second aspect, provided is an ophthalmic formulation, comprising an active agent, and a n≥40 polyoxyl lipid or fatty acid. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 0.5 and 2%, or 0.7 and 2%, or 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In a third aspect, provided is an ophthalmic formulation, that includes an active ingredient (such as a hydrophobic active ingredient) and a polyoxyl lipid or fatty acid; wherein said polyoxyl lipid or fatty acid is present in an amount equal to or greater than 1% of said formulation. In a similar aspect, provided is an ophthalmic formulation, that includes an active ingredient (such as a hydrophobic active ingredient) and a polyoxyl lipid or fatty acid; wherein said polyoxyl lipid or fatty acid is present in an amount equal to or greater than 0.05% of said formulation. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-60, HCO-80 or HCO-100) is present between 0.5 and 2%, or 0.7 and 2%, or between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In a fourth aspect, provided is an ophthalmic formulation, that includes an active agent and a polyoxyl lipid or fatty acid; wherein said formulation comprises nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 0.5 and 2%, or 0.7 and 2%, or between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In a further aspect provided is an ophthalmic formulation, comprising an active agent, 1-5% of one or more selected from the group consisting of HCO-40, HCO-60, HCO-80 and HCO-100; and about 0.01% octoxynol-40.

In another aspect, provided is ophthalmic formulation, comprising an active agent, 1-5% of one or more selected from the group consisting of HCO-40, HCO-60, HCO-80 and HCO-100; and about 0.01% octoxynol-40.

In yet another aspect, provided is an ophthalmic formulation, comprising an active agent, 1-5% of one or more selected from the group consisting of HCO-40, HCO-60, HCO-80 and HCO-100; and about 0.01% octoxynol-40.

In one aspect, provided is an ophthalmic formulation, comprising an active agent, 1-5% of one or more selected from the group consisting of HCO-40, HCO-60, HCO-80 and HCO-100; and about 0.01% octoxynol-40.

In a further aspect provided is an ophthalmic formulation, comprising an active agent, about 4% of HCO-60 and about 0.01% octoxynol-40.

In another aspect provided is an ophthalmic formulation, comprising an active agent, 0.7-1.5% of one or more selected from the group consisting of HCO-40, HCO-60, HCO-80 and HCO-100; and about 0.05% octoxynol-40.

In another aspect, provided is ophthalmic formulation, comprising an active agent, 0.7-1.5% of one or more selected from the group consisting of HCO-40, HCO-60, HCO-80 and HCO-100; and about 0.05% octoxynol-40.

In yet another aspect, provided is an ophthalmic formulation, comprising an active agent, 0.7-1.5% of one or more selected from the group consisting of HCO-40, HCO-60, HCO-80 and HCO-100; and about 0.05% octoxynol-40.

In one aspect, provided is an ophthalmic formulation, comprising an active agent, 0.7-1.5% of one or more selected from the group consisting of HCO-40, HCO-60, HCO-80 and HCO-100; and about 0.05% octoxynol-40.

In a further aspect provided is an ophthalmic formulation, comprising an active agent, about 1% of HCO-60 and about 0.05% octoxynol-40.

In various embodiments of any of the aspects and embodiments described herein, the formulation includes nanomicelles.

In some embodiments of the aspects and embodiments described herein, the formulation includes a polyoxyl lipid or fatty acid. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-60, HCO-80 or HCO-100) is present between 0.5 and 2%, or 0.7 and 2%, or 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100.

In some embodiments of the aspects and embodiments disclosed herein, includes a polyalkoxylated alcohol. In some embodiments, the formulation includes a polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In some embodiments, the active ingredient is cyclosporine A.

The instant disclosure further relates to treating or preventing ocular diseases or disorders, for example by local administration of the formulations as described herein.

A patient or subject to be treated by any of the compositions or methods of the present disclosure can mean either a human or a non-human animal. In an embodiment, the present disclosure provides methods for the treatment of an ocular disease in a human patient in need thereof. In an embodiment, the present disclosure provides methods for the treatment of an inflammatory ocular disease in a human patient in need thereof. In another embodiment, the present disclosure provides methods for the treatment of an ocular disease in a veterinary patient in need thereof, including, but not limited to dogs, horses, cats, rabbits, gerbils, hamsters, rodents, birds, aquatic mammals, cattle, pigs, camelids, and other zoological animals.

In some embodiments of the compositions and methods disclosed herein, the active agent includes a combination of two or more different active ingredients. In some embodiments the active agent includes two or more active agents selected from the group consisting of a resolvin or resolvin-like compound, a steroid (such as a corticosteroid), cyclosporine A, and voclosporin. In some embodiments the active agent includes a resolvin and cyclosporine A. In some embodiments the active agent includes cyclosporine A and a corticosteroid. In some embodiments, the active agent includes a resolvin, cyclosporine A and a corticosteroid. In some embodiments, the active agent includes two or more active agents and one of said active agents is an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the active agent includes two or more active agents and one of the active agents is an antibiotic, for example one or more antibiotics selected from the group consisting of azythromycin, ciprofloxacin, ofloxacin, gatifloxacin, levofloxacin, moxifloxacin, besifloxacin, and levofloxacin; and a second of such agents is a resolvin such as described herein (including without limitation compound 1001). In some embodiments, the active agent includes two or more active agents and one of said active agents is an antiviral, for example one or more antivirals selected from the group consisting of ganciclovir, trifluridine, acyclovir, famciclovir, valacyclovir, penciclovir and cidofovir. In some embodiments, the active agent includes two or more active agents and one of the active agents is an antibiotic, for example one or more antivirals selected from the group consisting of ganciclovir, trifluridine, acyclovir, famciclovir, valacyclovir, penciclovir and cidofovir; and a second of the active agents is a resolvin such as described herein (including without limitation compound 1001).

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and/or relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the terms "ocular disease," "ocular condition," "eye disease," and "eye condition" refer to diseases/conditions of the eye(s) that can be sight threatening, lead to eye discomfort, and may signal systemic health problems.

As used herein, the term "anterior segment disease" refers to all disorders that affect the eye surface, anterior chamber, iris and ciliary body and lens of the eye. The eye surface is composed of the cornea, conjunctiva, eyelids, lacrimal and meibomian glands, and the interconnecting nerves.

As used herein, the terms "posterior segment eye disease" and "back-of-the-eye disease" refer to all disorders that affect the posterior segment of the eye. A posterior eye disease is a disease which primarily affects a posterior ocular site such as choroid or sclera, vitreous, vitreous chamber, retina, optic nerve, and blood vessels and nerves which vascularize or innervate a posterior ocular site.

Accordingly, in one aspect, provided is a method treating or preventing an ocular disease or condition, that includes locally administering a formulation of any of the aspects or embodiments as disclosed herein. In some embodiments, the ocular disease is an anterior segment disease. In some embodiments, the ocular disease is a posterior segment disease. In some embodiments, the ocular disease is one or more selected from the group consisting of dry eye syndrome, Sjogren's syndrome, uveitis, anterior uveitis (iritis), chorioretinitis, posterior uveitis, conjunctivitis, allergic conjunctivitis, keratitis, keratoconjunctivitis, vernal keratoconjunctivitis (VKC), atopic keratoconjunctivitis, systemic immune mediated diseases such as cicatrizing conjunctivitis and other autoimmune disorders of the ocular surface, blepharitis, scleritis, age-related macular degeneration (AMD), diabetic retinopathy (DR), diabetic macular edema (DME), ocular neovascularization, age-related macular degeneration (ARMD), proliferative vitreoretinopathy (PVR), cytomegalovirus (CMV) retinitis, optic neuritis, retrobulbar neuritis, and macular pucker. In one embodiment, the ocular disease is dry eye. In one embodiment, the ocular disease is allergic conjunctivitis. In one embodiment the ocular disease is age-related macular degeneration (AMD). In one embodiment the ocular disease is diabetic retinopathy.

DETAILED DESCRIPTION OF THE PREFERRED EMBODIMENTS

Active Agents

In accordance various aspects and embodiments of the methods and compositions provided herein, an active agent can be any agent capable of affecting a biological process. Active agents (the term active ingredient is used herein interchangably with the term active agent) include drugs, hormones, cytokines, toxins, therapeutic agents, vitamins and the like. In some embodiments an active agent in accordance with the aspects and embodiments disclosed herein is an agent capable of, or approved for, treating or preventing an disease or condition, for example in some embodiments an active agent is capable of, or approved for, treating or preventing an ocular disease or condition.

In some embodiments, the active agent is an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the active agent is an antiviral, for example one or more antivirals selected from the group consisting of ganciclovir, trifluridine, acyclovir, famciclovir, valacyclovir, penciclovir and cidofovir.

In some embodiments of any of the aspects and embodiments disclosed herein, the active agent may be a calcineurin inhibitor such as cyclosporine A, voclosporin, ascomycin, tacrolimus, pimecrolimus, an analog thereof, or a pharmaceutically acceptable salt thereof.

A calcineurin inhibitor of the present disclosure is preferably an immunophilin-binding compound having calcineurin inhibitory activity. Immunophilin-binding calcineurin inhibitors are compounds forming calcineurin inhibiting complexes with immunophilins, e.g. cyclophilin and macrophilin. Examples of cyclophilin-binding calcineurin inhibitors are cyclosporines or cyclosporine derivatives (hereinafter cyclosporines) and examples of macrophilin-binding calcineurin inhibitors are ascomycin (FR 520) and ascomycin derivatives (hereinafter ascomycins). A wide range of ascomycin derivatives are known, which are either naturally occurring among fungal species or are obtainable by manipulation of fermentation procedures or by chemical derivatization. Ascomycin-type macrolides include ascomycin, tacrolimus (FK506), sirolimus and pimecrolimus.

Cyclosporine, originally extracted from the soil fungus Potypaciadium infilatum, has a cyclic 11-amino acid structure and includes e.g. Cyclosporines A through I, such as Cyclosporine A, B, C, D and G. Cyclosporine binds to the cytosolic protein cyclophilin of immunocompetent lymphocytes, especially T-lymphocytes, forming a complex. The complex inhibits calcineurin, which under normal circumstances induces the transcription of interleukin-2 (IL-2). Cyclosporine also inhibits lymphokine production and interleukin release, leading to a reduced function of effector T-cells.

Ocular Diseases

In various aspects and embodiments the formulations as disclosed herein may be used to treat or prevent an ocular disease or disorder. Ocular diseases and disorders contemplated herein include anterior segment diseases and posterior segment diseases. Exemplary ocular diseases that may in certain embodiments be treated with formulations as disclosed herein include the following.

Dry eye syndrome (DES, Chronic dry eye, Keratitis sicca; Xerophthalmia; Keratoconjunctivitis sicca) can be defined as a condition that includes a variety of disorders that result in a loss of, or altered composition of, the natural tear film, which maintains the surface of the eye. Without this tear film, vision is impaired and patients may suffer severe ocular discomfort. DES can be caused by excessive tear evaporation or by a reduction of tear production in the lacrimal gland, which is the site of tear production. Though the exact causes of this condition are unknown, there is evidence supporting the link between reduced tear production and inflammation of one or more components of the lacrimal apparatus. Currently available medications for DES are leaving substantial room for more effective and better tolerated products.

DES may also be a manifestation of Sjogren's syndrome which is an autoimmune disorder in which the glands that produce tears and saliva are destroyed. This leads to dry mouth, decreased tearing, and other dry mucous membranes.

Noninfectious uveitis is a chronic inflammatory, putative Th1/Th17-mediated autoimmune disease associated with substantial visual morbidity and is potentially blinding. Blindness from uveitis usually does not occur from a single inflammatory episode; rather, cumulative damage results from recurrent episodes of inflammation. The inflammatory sequelae resulting in vision loss may include one or more of cystoid macular edema, cataracts, vitreous debris, glaucoma, macular pathology (scarring and atrophy), optic neuropathy, and retinal detachment.

Anterior uveitis (iritis) occurs in the front of the eye and is the most common form of uveitis. Par planitis is an inflammation of the pars plana, a narrow area between the iris and the choroid. This condition occurs more frequently in young men, but is usually not associated with another disease. Posterior uveitis (chondroitis) affects primarily the choroid; the back portion of the uveal tract. If the retina is also involved, it is called chorioretinitis. Posterior uveitis may occur in association with an autoimmune disease, or follow a systemic infection. In posterior uveitis, inflammation can last from months to years and may cause permanent vision damage, even with treatment.

Uveitis can cause vision impairment, ocular pain, and loss of vision. It is estimated that about 10% of new cases of blindness in the U.S. are caused by uveitis. Approximately 300,000 people suffer from uveitis in the U.S. alone, the majority of whom are affected by anterior uveitis. The only therapeutic class approved by the FDA for treatment of uveitis is corticosteroids, which are noted for multiple side effects, such as hypertension, hyperglycemia, and hypercholesterolemia, and in the eye, glaucoma and cataract formation.

Conjunctivitis (pink eye) describes a group of diseases that cause swelling, itching, burning, and redness of the conjunctiva, the protective membrane that lines the eyelids and covers exposed areas of the sclera, or white of the eye.

Keratitis is an inflammation of the cornea (clear portion in the front of the eye). Keratitis can be caused by an infection (bacterial, fungal, viral, parasite, etc.) or a non-infectious agent (e.g., certain types of auto-immune diseases are associated with a variety of non-infectious keratitises).

Keratoconjunctivitis refers to an inflammation of the cornea and conjunctiva.

Vernal keratoconjunctivitis (VKC) is a recurrent ocular inflammatory disease characterized by hard, elevated, cobblestone like bumps on the upper eyelid. There may also be swellings and thickening of the conjunctiva. The conjunctiva is the outermost membrane which lines the eyelids as well as the exposed parts of the eye, except for the cornea.

Atopic keratoconjunctivitis is the result of a condition called atopy. Atopy is a genetic condition whereby the immune system produces higher than normal antibodies in response to a given allergen.

Systemic immune mediated diseases such as cicatrizing conjunctivitis and other autoimmune disorders of the ocular surface represent a clinically heterogeneous group of conditions where acute and chronic autoreactive mechanisms can cause significant damage to the eye. When severe and affecting the epithelium and substantia propria of the conjunctiva, cicatrization can ensue, leading to significant mechanical alterations as a result of the fibrosis. These conditions, though generally infrequent, can be the cause of profound pathology and visual disability.

Blepharitis is a common condition that causes inflammation of the eyelids.

Scleritis is a serious inflammatory disease that affects the white outer coating of the eye, known as the sclera.

Age-related macular degeneration (AMD) is a disease associated with aging that gradually destroys sharp, central vision. AMD affects the macula, which is located at the center of the retina. AMD occurs in two forms: wet and dry. Wet AMD occurs when abnormal blood vessels behind the retina start to grow under the macula. These new blood vessels tend to be very fragile and often leak blood and fluid. The blood and fluid raise the macula from its normal place at the back of the eye. Damage to the macula occurs rapidly. Dry AMD occurs when the light-sensitive cells in the macula slowly break down, gradually blurring central vision in the affected eye.

Diabetes can affect the eye in a number of ways. Diabetic retinopathy (DR) is a complication of diabetes that results from damage to the blood vessels of the light-sensitive tissue at the back of the eye (the retina). At first, diabetic retinopathy may cause no symptoms or only mild vision problems. Eventually, however, diabetic retinopathy can result in blindness. Diabetic macular edema (DME) is the swelling of the retina in diabetes mellitus due to leaking of fluid from blood vessels within the macula.

Ocular neovascularization is the abnormal or excessive formation of blood vessels in the eye. Ocular neovascularization has been shown in diabetic retinopathy and age-related macular degeneration (AMD).

Proliferative vitreoretinopathy (PVR) is scar tissue formation within the eye. "Proliferative" because cells proliferate and "vitreoretinopathy" because the problems involve the vitreous and retina. In PVR scar tissue forms in sheets on the retina which contract. This marked contraction pulls the retina toward the center of the eye and detaches and distorts the retina severely. PVR can occur both posteriorly and anteriorly with folding of the retina both anteriorly and circumferentially.

The cytomegalovirus (CMV) is related to the herpes virus and is present in almost everyone. When a person's immune system is suppressed because of disease (HIV), organ or bone marrow transplant, or chemotherapy, the CMV virus can cause damage and disease to the eye and the rest of the body. CMV affects the eye in about 30% of the cases by causing damage to the retina. This is called CMV retinitis.

Optic neuritis occurs when the optic nerve becomes inflamed and the myelin sheath becomes damaged or is destroyed. Nerve damage that occurs in the section of the optic nerve located behind the eye, is called retrobulbar neuritis, which is another term sometimes used for optic neuritis.

Also known as macular pucker, epiretinal membrane is a scar-tissue like membrane that forms over the macula. It typically progresses slowly and affects central vision by causing blurring and distortion. As it progresses, the pulling of the membrane on the macula may cause swelling.

In an embodiment, the compositions can be used for preventing transplant rejection of, for example, corneal allografts following transplantation. It is well known that in inflammation T-lymphocytes play a critical role in mediating rejection of foreign tissues. Prevention of rejection is of paramount importance in maintaining the health of transplanted corneas. Rejection may occur in any of the layers comprising the cornea, for example, the corneal epithelium, the corneal stroma or the corneal endothelium. The functioning of the cornea can be compromised following endothelial rejection. The endothelial layer serves to maintain the cornea in a compact state, acting as a pump by removing water from the corneal stroma. If the function of the endothelial layer is compromised, disorientation of collagen fibers can ensue, and transparency of the cornea can be lost. Human endothelial cells are non-replicative, and as a consequence, donor cell loss in the setting of rejection is irreversible and may lead to diminished graft function and survival. Thus, the goal of either prevention or treatment of rejection in corneal transplant recipients is to minimize endothelial cell loss. The compositions of the present disclosure can be used for the prevention of rejection following corneal allograft transplantation.

Additional Formulation Ingredients

The compositions of the present disclosure may also contain other components such as, but not limited to, additives, adjuvants, buffers, tonicity agents, bioadhesive polymers, and preservatives. In any of the compositions of this disclosure for topical to the eye, the mixtures are preferably formulated at about pH 5 to about pH 8. This pH range may be achieved by the addition of buffers to the composition as described in the examples. In an embodiment, the pH range in the composition in a formulation is about pH 6.6 to about pH 7.0. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values. The mixed micellar compositions of the present disclosure are stable in buffered aqueous solution. That is, there is no adverse interaction between the buffer and any other component that would cause the compositions to be unstable.

Tonicity agents include, for example, mannitol, sodium chloride, xylitol, etc. These tonicity agents may be used to adjust the osmolality of the compositions. In one aspect, the osmolality of the formulation is adjusted to be in the range of about 250 to about 350 mOsmol/kg. In a preferred aspect, the osmolality of the formulation is adjusted to between about 280 to about 300 mOsmol/kg.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the calcineurin inhibitor or mTOR inhibitor, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose. In an embodiment, the sugars can be incorporated into a composition prior to hydrating the thin film (i.e., internally). In another embodiment, the sugars can be incorporated into a composition during the hydration step (i.e., externally) (see Example 17). In an embodiment, an aqueous, clear, mixed micellar solution of the present disclosure includes additives such as sugars.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight. Bioadhesion systems have been used in dentistry, orthopedics, ophthalmology, and in surgical applications. However, there has recently emerged significant interest in the use of bioadhesive materials in other areas such as soft tissue-based artificial replacements, and controlled release systems for local release of bioactive agents. Such applications include systems for release of drugs in the buccal or nasal cavity, and for intestinal or rectal administration.

In an embodiment, a composition of the present disclosure includes at least one bioadhesive polymer. The bioadhesive polymer can enhance the viscosity of the composition and thereby increase residence time in the eye. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medications to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil. In an embodiment, the polymer excipient is selected from PVP-K-90, PVP-K-30 or HPMC. In an embodiment, the polymer excipient is selected from PVP-K-90 or PVP-K-30.

In an embodiment, if a preservative is desired, the compositions may optionally be preserved with any of many well-known preservatives, including benzyl alcohol with/without EDTA, benzalkonium chloride, chlorhexidine, Cosmocil® CQ, or Dowicil® 200. In certain embodiments, it may be desirable for a formulation as described herein to not include any preservatives. In this regard, preservatives may in some embodiments not be necessary or desirable in formulations included in single use containers. In other embodiments it may be advantageous to include preservatives, such as in certain embodiments in which the formulations are included in a multiuse container.

The ophthalmic compositions can be administered topically to the eye as biocompatible, aqueous, clear mixed micellar solutions. The compositions have the drugs incorporated and/or encapsulated in micelles which are dispersed in an aqueous medium.

Non-Limiting List of Exemplary Embodiments

In addition to the aspects and embodiments described and provided elsewhere in this disclosure, the following non-limiting list of particular embodiments are specifically contemplated.

1. An ophthalmic formulation, comprising an active agent, a polyoxyl lipid or fatty acid and a polyalkoxylated alcohol.

2. An ophthalmic formulation, comprising an active agent, and a n≥40 polyoxyl lipid or fatty acid.

3. An ophthalmic formulation, comprising an active ingredient and a polyoxyl lipid or fatty acid; wherein said polyoxyl lipid or fatty acid is present in an amount equal to or greater than 1% of said formulation.

4. An ophthalmic formulation, comprising an active agent and a polyoxyl lipid or fatty acid; wherein said formulation comprises nanomicelles.

5. An ophthalmic formulation, comprising an active agent, 1-5% of one or more selected from the group consisting of HCO-40, HCO-60, HCO-80 and HCO-100; and about 0.01-0.1% octoxynol-40.

6. An ophthalmic formulation, comprising an active agent, 1-5% of one or more selected from the group consisting of HCO-40, HCO-60, HCO-80 and HCO-100; and about 0.01-0.1% octoxynol-40.

7. An ophthalmic formulation, comprising greater than 0.2% of an active agent, 1-5% of one or more selected from the group consisting of HCO-40, HCO-60, HCO-80 and HCO-100; and about 0.01-0.1% octoxynol-40.

8. An ophthalmic formulation, comprising an active agent, 1.5-4% of one or more polyoxl lipids selected from the group consisting of HCO-40, HCO-60, HCO-80 and HCO-100; and about 0.01-0.1% octoxynol-40.

9. An ophthalmic formulation, comprising an active agent, 1.5-4% of polyoxl lipids or fatty acids; and about 0.01-0.1% octoxynol-40.

10. An ophthalmic formulation, comprising an active agent, 1.5-4% of polyoxl lipids or fatty acids; and about 0.01-0.1% octoxynol-40; wherein the formulation comprises nanomicelles.

11. An ophthalmic formulation, comprising a hydrophobic active agent, 1.5-4% of polyoxl lipids or fatty acids; and about 0.01-0.1% octoxynol-40; wherein the formulation comprises nanomicelles.

12. An ophthalmic formulation, comprising an active agent, about 4% of one or more selected from the group consisting of HCO-40, HCO-60, HCO-80 and HCO-100; and about 0.01-0.1% octoxynol-40.

13. An ophthalmic formulation, comprising an active agent, about 4% of HCO-60 and about 0.01-0.1% octoxynol-40.

14. An ophthalmic formulation, comprising an active agent, 1-5% of one or more selected from the group consisting of HCO-40, HCO-60, HCO-80 and HCO-100; and about 0.01% octoxynol-40.

15. An ophthalmic formulation, comprising an active agent, 1-5% of one or more selected from the group consisting of HCO-40, HCO-60, HCO-80 and HCO-100; and about 0.01% octoxynol-40.

16. An ophthalmic formulation, comprising greater than 0.2% of an active agent, 1-5% of one or more selected from the group consisting of HCO-40, HCO-60, HCO-80 and HCO-100; and about 0.01% octoxynol-40.

17. An ophthalmic formulation, comprising an active agent, 1.5-4% of one or more polyoxl lipids selected from the group consisting of HCO-40, HCO-60, HCO-80 and HCO-100; and about 0.01% octoxynol-40.

18. An ophthalmic formulation, comprising an active agent, 1.5-4% of polyoxl lipids or fatty acids; and about 0.01% octoxynol-40.

19. An ophthalmic formulation, comprising an active agent, 1.5-4% of polyoxl lipids or fatty acids; and about 0.01% octoxynol-40; wherein the formulation comprises nanomicelles.

20. An ophthalmic formulation, comprising a hydrophobic active agent, 1.5-4% of polyoxl lipids or fatty acids; and about 0.01% octoxynol-40; wherein the formulation comprises nanomicelles.

21. An ophthalmic formulation, comprising an active agent, about 4% of one or more selected from the group consisting of HCO-40, HCO-60, HCO-80 and HCO-100; and about 0.01% octoxynol-40.

22. An ophthalmic formulation, comprising an active agent, about 4% of HCO-60 and about 0.01% octoxynol-40.

23. The formulation of any of the preceding embodiments, wherein said polyoxyl lipid or fatty acid is between 0.5 and 6% by weight of said formulation.

24. The formulation of any of the preceding embodiments, wherein said polyoxyl lipid or fatty acid is between 0.5 and 2% by weight of said formulation.

25. The formulation of any of the preceding embodiments, wherein said polyoxyl lipid or fatty acid is between 0.5 and 3% by weight of said formulation.

26. The formulation of any of the preceding embodiments, wherein said polyoxyl lipid or fatty acid is between 0.5 and 4% by weight of said formulation.

27. The formulation of any of the preceding embodiments, wherein said polyoxyl lipid or fatty acid is between 0.5 and 5% by weight of said formulation.

28. The formulation of any of the preceding embodiments, wherein said polyoxyl lipid or fatty acid is between 1 and 6% by weight of said formulation.

29. The formulation of any of the preceding embodiments, wherein said polyoxyl lipid or fatty acid is between 1 and 2% by weight of said formulation.

30. The formulation of any of the preceding embodiments, wherein said polyoxyl lipid or fatty acid is between 1 and 3% by weight of said formulation.

31. The formulation of any of the preceding embodiments, wherein said polyoxyl lipid or fatty acid is between 1 and 4% by weight of said formulation.

32. The formulation of any of the preceding embodiments, wherein said polyoxyl lipid or fatty acid is between 1 and 5% by weight of said formulation.

33. The formulation of any of the preceding embodiments, wherein said polyoxyl lipid or fatty acid is between 1 and 6% by weight of said formulation.

34. The formulation of any of the preceding embodiments, wherein said polyoxyl lipid or fatty acid is between 2 and 6% by weight of said formulation.

35. The formulation of any of the preceding embodiments, wherein said polyoxyl lipid or fatty acid is between 3 and 6% by weight of said formulation.

36. The formulation of any of the preceding embodiments, wherein said polyoxyl lipid or fatty acid is between 4 and 6% by weight of said formulation.

37. The formulation of any of the preceding embodiments, wherein said polyoxyl lipid or fatty acid is between 2 and 5% by weight of said formulation.

38. The formulation of any of the preceding embodiments, wherein said polyoxyl lipid or fatty acid is between 3 and 5% by weight of said formulation.

39. The formulation of any of the preceding embodiments, wherein said polyoxyl lipid or fatty acid is about 4% by weight of said formulation.

40. The formulation of any of the preceding embodiments, wherein said polyoxyl lipid or fatty acid is greater than about 0.7% by weight of said formulation.

41. The formulation of any of the preceding embodiments, wherein said polyoxyl lipid or fatty acid is greater than about 1% by weight of said formulation.

42. The formulation of any of the preceding embodiments, wherein said polyoxyl lipid or fatty acid is greater than about 1.5% by weight of said formulation.

43. The formulation of any of the preceding embodiments, wherein said polyoxyl lipid or fatty acid is greater than about 2% by weight of said formulation.

44. The formulation of any of the preceding embodiments, wherein said polyoxyl lipid or fatty acid is greater than about 3% by weight of said formulation.

45. The formulation of any of the preceding embodiments, wherein said polyalkoxylated alcohol if present is between 0.002 and 4% by weight of said formulation.

46. The formulation of any of the preceding embodiments, wherein said polyalkoxylated alcohol if present is between 0.005 and 3% by weight of said formulation.

47. The formulation of any of the preceding embodiments, wherein said polyalkoxylated alcohol if present is between 0.005 and 2% by weight of said formulation.

48. The formulation of any of the preceding embodiments, wherein said polyalkoxylated alcohol if present is between 0.005 and 1% by weight of said formulation.

49. The formulation of any of the preceding embodiments, wherein said polyalkoxylated alcohol if present is between 0.005 and 0.5% by weight of said formulation.

50. The formulation of any of the preceding embodiments, wherein said polyalkoxylated alcohol if present is between 0.005 and 0.1% by weight of said formulation.

51. The formulation of any of the preceding embodiments, wherein said polyalkoxylated alcohol if present is between 0.005 and 0.05% by weight of said formulation.

52. The formulation of any of the preceding embodiments, wherein said polyalkoxylated alcohol if present is between 0.008 and 0.02% by weight of said formulation.

53. The formulation of any of the preceding embodiments, wherein said polyalkoxylated alcohol if present is about 0.01% by weight of said formulation.

54. The formulation of any of the preceding embodiments, wherein said active ingredient is present in said formulation in an amount greater than 0.2%.

55. The formulation of any of the preceding embodiments, wherein said active ingredient is present in said formulation in an amount greater than 0.3%.

56. The formulation of any of the preceding embodiments, wherein said active ingredient is present in said formulation in an amount greater than 0.4%.

57. The formulation of any of the preceding embodiments, wherein said active ingredient is present in said formulation in an amount greater than 0.5%.

58. The formulation of any of the preceding embodiments, wherein said active ingredient is present in said formulation in an amount greater than 0.6%.

59. The formulation of any of the preceding embodiments, wherein said active ingredient is present in said formulation in an amount greater than 0.7%.

60. The formulation of any of the preceding embodiments, wherein said active ingredient is present in said formulation in an amount greater than 0.8%.

61. The formulation of any of the preceding embodiments, wherein said active ingredient is present in said formulation in an amount greater than 0.9%.

62. The formulation of any of the preceding embodiments, wherein said active ingredient is present in said formulation in an amount greater than 1%.

63. The formulation of any of the preceding embodiments, wherein said active ingredient is present in said formulation in an amount greater than 1.5%.

64. The formulation of any of the preceding embodiments, wherein said active ingredient is present in said formulation in an amount greater than 2%.

65. The formulation of any of the preceding embodiments, wherein said active ingredient is present in said formulation in an amount greater than 3%.

66. The formulation of any of the preceding embodiments, wherein said active ingredient is present in said formulation in an amount greater than 4%.

67. The formulation of any of the preceding embodiments, wherein said polyoxyl lipid or fatty acid is a polyoxyl castor oil.

68. The formulation of any of the preceding embodiments, wherein said polyoxyl lipid or fatty acid is one or more selected from HCO-60, HCO-80 or HCO-100.

69. The formulation of any of the preceding embodiments, wherein said polyoxyl lipid or fatty acid is HCO-60.

70. The formulation of any of the preceding embodiments, wherein said active agent is one or more selected from the group consisting of cyclosporine A, voclosporin, ascomycin, tacrolimus, pimecrolimus, an analog thereof, or a pharmaceutically acceptable salt thereof.

71. The formulation of any of the preceding embodiments, wherein said active agent is cyclosporine A.

72. The formulation of any of the preceding embodiments, wherein said active agent is voclosporin.

73. The formulation of any of the preceding embodiments, wherein said active agent comprises a combination of two different agents.

74. The formulation of any of the preceding embodiments, wherein the active agent comprises two or more active agents selected from the group consisting of a resolvin or resolvin-like compound, a steroid (such as a corticosteroid), cyclosporine A, and voclosporin.

75. The formulation of any of the preceding embodiments, wherein the active agent comprises a resolvin and a corticosteroid.

76. The formulation of any of the preceding embodiments, wherein the active agent comprises cyclosporine A and a corticosteroid.

77. The formulation of any of the preceding embodiments, wherein the active agent comprises a resolvin, cyclosporine A and a corticosteroid.

78. The formulation of any of the preceding embodiments, wherein said formulation does not include preservatives.

79. The formulation of any of the preceding embodiments, wherein said formulation does not include benzyl alcohol with/without EDTA, benzalkonium chloride, chlorhexidine, Cosmocil® CQ, or Dowicil® 200.

80. A method of treating or preventing an ocular disease or condition, said method comprising topically administering a formulation of any of the preceding embodiments.

81. A method of treating or preventing an ocular disease or condition, said method comprising topically administering a formulation of any of the preceding embodiments; wherein said disease is an anterior segment disease.

82. A method of treating or preventing an ocular disease or condition, said method comprising topically administering a formulation of any of the preceding embodiments; wherein said disease is an posterior segment disease.

83. A method of treating or preventing an ocular disease or condition, said method comprising topically administering a formulation of any of the preceding embodiments; wherein said disease is one or more selected from the group consisting of dry eye syndrome, Sjogren's syndrome, uveitis, anterior uveitis (iritis), chorioretinitis, posterior uveitis, conjunctivitis, allergic conjunctivitis, keratitis, keratoconjunctivitis, vernal keratoconjunctivitis (VKC), atopic keratoconjunctivitis, systemic immune mediated diseases such as cicatrizing conjunctivitis and other autoimmune disorders of the ocular surface, blepharitis, scleritis, age-related macular degeneration (AMD), diabetic retinopathy (DR), diabetic macular edema (DME), ocular neovascularization, age-related macular degeneration (ARMD), proliferative vitreoretinopathy (PVR), cytomegalovirus (CMV) retinitis, optic neuritis, retrobulbar neuritis, and macular pucker.

84. A method of treating or preventing an ocular disease or condition, said method comprising topically administering a formulation of any of the preceding embodiments; wherein said disease is dry eye syndrome.

85. A method of treating or preventing an ocular disease or condition, said method comprising topically administering a formulation of any of the preceding embodiments; wherein said disease is allergic conjunctivitis.

86. A method of treating or preventing an ocular disease or condition, said method comprising topically administering a formulation of any of the preceding embodiments; wherein said disease is age-related macular degeneration (AMD).

The following examples are provided to further illustrate aspects of the invention. These examples are non-limiting and should not be construed as limiting any aspect of the invention.

Example 1

Preparation of Mixed Nanomicellar Resolvin Formulation Using Dialysis Method

Mixed nanomicellar formulation of compound 1001 was prepared by dialysis method with varying ratio of polymers and the drug. Experimental design software, JMP 9.0 was used to design the experiments and analyze the results. Accurately weighted quantities of two polymers namely polyoxyl hydrogenated castor-60 (HCO-60) and octoxynol-40 (Oc-40) were dissolved in 300 microliter volume of propylene glycol. Eighty microliter (or 80 mg of compound 1001 in PG) of propylene glycol containing compound 1001 was added to this polymer mixture and vortex mixed to get a clear homogenous solution. The volume of the mixture was made up (500 microliters) with propylene glycol. The solution was vortex mixed to get a homogenous solution. A volume of 500 microliter distilled deionized water was added to this mixture to obtain a total volume of 1000 microliter (1 milliliter). Addition of water to the drug polymer mixture in organic solvent should spontaneously generate micelles thereby entrapping the pharmaceutical active agent in the hydrophobic core of mixed nanomicelles. The mixture was transferred to a dialysis bag (molecular weight cut off 1000) and transferred to a beaker containing one liter of distilled deionized water. Beaker and the contents were protected from sunlight by covering with aluminum foil and were kept under slow constant stirring at room temperature. Dialysis of the mixture was carried over a period of 24 h to remove the water soluble organic solvent, propylene glycol, from the mixture. Water in the dialysis chamber was changed at predetermined time points: 1 h, 2 h, 4 h, 6 h, 12 h and 24 h. At the end of dialysis (24 h), the contents of the dialysis bag were carefully transferred to a 15-mL centrifuge tube and formulations were subjected to sonication in water bath (time range from 0 min to 5 min). The final volume was made up with 2× phosphate buffer saline and adjusted pH of the formulation to 6.5±0.1. The resultant formulation was filtered with 0.22 micrometer nylon filter to remove any foreign particulate matter.

The prepared formulations were subjected to various tests such as entrapment efficiency, loading efficiency, mixed nanomicellar size and polydispersity index.

Mixed Nanomicellar Size and Polydispersity Index:

The formulation size and polydispersity index were determined with Zetasizer, Malvern Instruments, NJ. In brief, approximately 1 ml of each formulation was transferred to a cuvette and placed in the instrument. A laser beam of light was used to determine the mixed nanomicellar size. The results of the size are summarized in Table 2.

Entrapment Efficiency:

To determine the entrapment efficiency of the formulation, all the prepared formulations were subjected to entrapment efficiency test. Briefly, formulations were vortex mixed for homogeneity and 1 mL was transferred to a fresh (1.5 mL) eppendorf tube. Each formulation was lyophilized to obtain a solid at the bottom of eppendorf tube. The obtained solid was suspended in 1 mL of organic solvent (diethyl ether) to generate reverse micelles and release the drug into the external organic solvent. The organic solvent was evaporated overnight in speed vacuum. The resultant reversed micelles were resuspended in 1 mL of 2-propanol (dilution factor was taken into account) and further diluted to determine the concentration of compound 1001 entrapped in each micellar preparation with HPLC. The entrapment efficiency of the formulation was calculated with the following formula (wherein MNF=Mixed Nanomicellar Formulation):

$$\text{Entrapment efficiency} = \frac{\text{(amount of drug quantified in } MNF\text{)}}{\text{Amount of drug added in the } MNF} \times 100$$

Drug Quantification by an HPLC Method:

In vitro analysis of compound 1001 was performed by a reversed phase high performance liquid chromatography (RP-HPLC) method with a Shimadzu HPLC pump (Shimadzu, Shimadzu Scientific instruments, Columbia, Md.), Alcott autosampler (model 718 AL), Shimadzu UV/Visible detector (Shimadzu, SPD-20A/20AV, USA), ODS column (5 µm, 150×4.6 mm) thermostated at 40°±1 C and Hewlett Packard HPLC integrator (Hewlett Packard, Palo Alto, Calif.). The mobile phase was comprised of methanol (MeOH), water and trifluoroacetic acid (TFA) (70:30:0.05% v/v) which was set at a flow rate of 0.5 mL/min. Detection wavelength was set at 272 nm. The sample tray temperature was maintained at 4° C. Calibration curve (0.5 to 5 µg/mL) for compound 1001 was prepared by making appropriate dilutions from the stock solution in 2-propanol. An injection volume of 10 µl was injected into the HPLC column for analysis. All the standards and samples prepared were stored at 4° C. before and during the analysis.

Example 2

Preparation of Mixed Nanomicellar Resolvin Formulation Using Ethyl Acetate Solvent Evaporation Method Mixed nanomicellar formulation encapsulating compound 1001 was prepared by solvent evaporation method in two steps: 1) Preparation of basic formulation and 2) rehydration. In step one, compound 1001, HCO-60 and octoxynol-40 were dissolved separately in 0.3 mL of ethyl acetate. These three solutions were mixed together in 15-mL centrifuge tube. The resultant mixture was vortexed to obtain a homogenous solution. Ethyl acetate solvent was removed with speed vacuum to obtain a solid thin film. The residue was kept overnight under high vacuum at room temperature to remove residual organic solvent. In step two, the resultant thin film was hydrated with 1 mL of double distilled deionized water by vortexing the solution. The rehydrated formulation was suspended in 2× phosphate buffer solution, (pH 6.5). It was filtered through 0.2 μm nylon filter membrane to remove the unentrapped drug aggregates and other foreign particulates. The entrapment of compound 1001 was determined by RP-HPLC following disruption of the micelles and solubilization of 1001 in the diluent (2-propanol) as described below The prepared formulations were subjected to various tests such as entrapment efficiency, loading efficiency, mixed nanomicellar size and polydispersity index according to the methods described in Example 1.

Weight percent of drug loaded into MNF was determined following the method for entrapment efficiency. Size and polydispersity index of the formulations was determined with Malvern zetasizer as described above. The results obtained are summarized in Table 1 below. The formulations appear clear and have small size and narrow size distribution.

was diluted 100 folds and allowed to equilibrate at 40 C for 1 h in water bath. Similarly, compound 1001 (neat oil) was allowed to equilibrate at 40 C in the water bath for 1 h. To the HCO-60 melt, 50 μL of 100 fold diluted octoxynol-40 (0.01 wt %) was added at 40 C. To the above mixture, ~20 μL of compound 1001 at 40 C was added and was stirred. To this mixture distilled deionized water, approx. 2 mL, equilibrated at 40 C was slowly added and stirred. The neck of the round bottom flask was closed with aluminum foil and sealed with parafilm. The solution was stirred in water bath set at 40 C overnight protected from light (covering with aluminum foil). On the next day, the above obtained solution at 40 C was removed from water bath and allowed to cool to room temperature and observed for clarity. Two milliliters phosphate buffer (2×) was added to the above prepared solution (phosphate buffer was previously prepared and the pH was adjusted to 5.5). The volume of the formulation was made up to 5 mL with the 2× phosphate buffer saline. The prepared formulation was filtered with 0.2 μm nylon filter and stored at 4 C.

The prepared formulations were subjected to various tests such as entrapment efficiency, loading efficiency, mixed nanomicellar size and polydispersity index according to the methods described in Example 1.

TABLE 1

Characterization of the mixed nanomicellar formulation encapsulating compound 1001 with solvent evaporation method

| HCO-60 (wt %) | Octoxynol-40 (wt %) | 1001 (initially added) wt % | 1001 (loaded in mixed micelles) wt % | Mixed nanomicellar size (nm) | Polydispersity Index | Result |
|---|---|---|---|---|---|---|
| 4 | 0.01 | 0.035 | 0.033 | 24.90 | 0.442 | Clear/transparent solution before and after filtration |
| 4 | 0.01 | 0.070 | 0.065 | 25.01 | 0.414 | Clear/transparent solution before and after filtration |
| 4 | 0.01 | 0.095 | 0.084 | 24.79 | 0.415 | Clear/transparent solution before and after filtration |
| 4 | 0.01 | 0.120 | 0.11 | 18.28 | 0.320 | Pale yellow color transparent solution before and after filtration |
| 4 | 0.01 | 0.250 | 0.26 | 18.37 | 0.331 | Yellow color solution before and after filtration |
| 4 | 0.01 | 0.300 | 0.32 | 18.29 | 0.345 | Yellow color |
| 4 | 0.01 | 0.400 | 0.45 | 18.2 | 0.333 | solution before and after filtration |

Example 3

Preparation of Mixed Nanomicellar Resolvin Formulation Using Melt Method

Two hundred milligrams of hydrogenated castor oil-60 (HCO-60) (4 wt %) was weighed and transferred to a 10 mL round bottom flask (RBF). The neck of the round bottom flask was closed with an aluminum foil, sealed with parafilm and transferred to water bath set at 40 C. The round bottom flask was left overnight in water bath to liquefy/melt the HCO-60. On the next day, ten micro liters of octoxynol-40

Example 4

Preparation of Mixed Nanomicellar Resolvin Formulation Using Second Melt Method

The preparation of MNF encapsulating compound 1001 (neat oil) can be divided into two steps. As an example for the development of 3.0 wt % HCO-40 or HCO-60 MNF encapsulating 0.4% compound 1001 is described below. In step 1, HCO-40 or HCO-60, 150 mg, was thermostated at 40° C. in water bath to melt and result in a clear thick viscous liquid. To this melt polymer compound 1001 (~20 mg), thermostated at 40° C., was added and mixed for homogenous distribution. The mixture was allowed to reach room temperature, which resulted in a pale yellow color viscous liquid with HCO-40 and waxy solid with HCO-60. Further, to solidify the viscous liquid of HCO-40, the mixture was stored at 4° C. (in refrigerator).

In step 2, the pellet and/or viscous liquid was allowed to reach room temperatures under natural conditions. The pellet and/or viscous liquid was thermostated in water bath at 40° C. and resuspended in 2.0 mL of distilled water (thermostated at 40° C.) under constant stirring. This resulted in spontaneous development of a clear aqueous solution of 0.4% compound 1001 MNF. This aqueous solution was allowed to reach room temperature, under natural conditions. The pH of the solution was adjusted to 5.5 and the volume was made up with 2× phosphate buffer saline (pH 5.5) containing octoxynol-40 (0.01 wt %) and PVP-K-90 (1.2 wt %). The formulation was filtered through 0.2 μm nylon filter to remove any foreign material and obtain a clear homogenous aqueous RX-1001 formulation.

$^1$H NMR Qualitative Studies:

To determine the absence of free drug in the outer aqueous environment, qualitative studies were conducted. Qualitative proton nuclear magnetic resonance (NMR) studies were conducted with Varian 400 MHz NMR. Deuterated chloroform and water as solvent systems were used to resuspend the formulation and NMR studies were performed.

Results:

Compound added to HCO-40 or HCO-60 at 40° C. can be used to entrap the compound 1001. At higher temperatures the polymer and the drug mixture remains in viscous liquid state. When allowed to reach room temperature, under natural conditions, HCO-60 mixture solidifies and develops a waxy solid. This waxy solid when thermostated at 40° C., helps in resuspending the formulation in distilled water to spontaneously develop compound 1001 MNF. Similar observation and results were obtained with HCO-40 viscous liquid. The viscosity of the mixture appears to be improved at lower temperatures (4° C.). Therefore, it appears to stick to the walls of the container as thick viscous liquid. Upon allowing to reach back to room temperature the viscosity appears to be reduced and the mixture retains its flow back.

The waxy solid developed with HCO-60 and compound 1001 mixture may be helpful to protect the drug and prevent the drug degradation with a surface blanket of an inert gas. The other polymer (HCO-40) did not result in development of waxy solid at room temperature or at low refrigerated conditions (4° C.) when used up to approx. 3.0 wt %.

Qualitative proton NMR studies show that resuspending the formulation in the aqueous phase (D$_2$O) spontaneously generated mixed nanomicelles and no free drug peaks were evident in the aqueous solution. If the drug was not entrapped in the core of mixed nanomicelles then the oil would be floating at the surface as a separate oil phase. While on the otherhand, resuspending the same formulation in organic solvent such as deuterated chloroform (CDCl$_3$) showed distinct peaks corresponding to drug along with polymer peaks. This indicates that the drug was not encapsulated in the micelle core and freely available when present in organic solvent.

The results obtained for physical appearance of the mixture, different phases, at different temperatures and appearance of final formulation are summarized in Tables 2a-2c.

TABLE 2a

Physical appearance of melt mixture of HCO-60 and Compound 1001 at 25° C., resuspending in water at 40°. and final formulation of mixed nanomicellar formulation encapsulating compound 1001 (HCO-60 was melted and compound 1001 was added to melt, then allowed to cool to room temperature and the physical appearance was noted)

| HCO-60 (wt %) | 1001 (wt %) | Physical appearance at room temperature (25° C.) | Resuspend in water | Final formulation (make up with 2X buffer containing 0.01% Oc-40) |
|---|---|---|---|---|
| 1.0 | 4 | Pale yellow half solid and half viscous liquid | Emulsion | Emulsion |
| 2.0 | 4 | Pale yellow viscous solid (with waxy and viscous liquid) | Forms pale emulsion | Pale yellow clear solution |
| 2.25 | 4 | Pale yellow waxy solid | Forms pale emulsion | Pale yellow clear solution |
| 2.5 | 4 | Pale yellow waxy solid | Forms very pale emulsion | Pale yellow clear solution |
| 2.75 | 4 | Pale yellow waxy solid | Forms very pale emulsion | Clear solution |
| 3.0 | 4 | Pale yellow waxy solid | Clear solution | Clear solution |
| 3.5 | 4 | Pale yellow waxy solid | Clear solution | Clear solution |
| 4.0 | 4 | Pale yellow waxy solid | Clear solution | Clear solution |

TABLE 2b

Physical appearance for HCO-40 and compound 1001 melt mixture at 25° C., resuspending in water and final formulation of mixed nanomicellar formulation encapsulating compound 1001 (HCO-40 was melted and compound 1001 was added to melt at 40° C. Then allowed to cool to room temperature and the physical appearance was noted)

| HCO-40 (wt %) | 1001 (wt %) | Mixture physical appearance at room temperature (25° C.) | Resuspend in water | Final formulation |
|---|---|---|---|---|
| 0.5 | 4 | Viscous yellow liquid | Emulsion | Emulsion |
| 0.75 | 4 | Viscous yellow liquid | Emulsion | Emulsion |
| 1.0 | 4 | Viscous yellow liquid | Emulsion | Emulsion |
| 1.25 | 4 | Viscous yellow liquid | Emulsion | Emulsion |
| 1.5 | 4 | Viscous yellow liquid | Emulsion | Emulsion |
| 1.75 | 4 | Viscous yellow liquid | Emulsion | Emulsion |
| 2.0 | 4 | Viscous yellow liquid | Emulsion | Emulsion |
| 2.25 | 4 | Viscous yellow liquid | Emulsion | Emulsion |
| 2.5 | 4 | Viscous yellow liquid | Yellow solution | Yellow color solution |
| 2.75 | 4 | Viscous yellow liquid | Pale yellow solution | Pale yellow color solution |
| 3.0 | 4 | Viscous yellow liquid | Clear solution | Clear solution |
| 4.0 | 4 | Viscous yellow liquid | Clear solution | Clear solution |

TABLE 2c

Physical appearance of HCO-40 and compound 1001 melt mixture at 25° C. and 4° C., mixture resuspended in water at 40° C. and final formulation. (HCO-40 was melted and compound 1001 was added to melt at 40° C. Then allowed to cool to room temperature, placed at 4° C. and brought back to room temperature. Physical appearance of mixture was noted at all temperatures)

| HCO-40 (wt %) | 1001 (wt %) | Mixture physical appearance at room temperature (25° C.) | Mixture physical appearance at room temperature (4° C.) | Allow to reach room temperature (25° C.) | Resuspend in water | Final formulation |
|---|---|---|---|---|---|---|
| 0.5 | 4 | Viscous yellow liquid | Viscous liquid | Viscous liquid | Emulsion | Emulsion |
| 0.75 | 4 | Viscous yellow liquid | Viscous liquid | Viscous liquid | Emulsion | Emulsion |
| 1.0 | 4 | Viscous yellow liquid | Viscous liquid | Viscous liquid | Emulsion | Emulsion |
| 1.25 | 4 | Viscous yellow liquid | Viscous liquid | Viscous liquid | Emulsion | Emulsion |
| 1.5 | 4 | Viscous yellow liquid | Yellow waxy solid | Viscous liquid | Emulsion | Emulsion |
| 1.75 | 4 | Viscous yellow liquid | Yellow waxy solid | Viscous liquid | Emulsion | Emulsion |
| 2.0 | 4 | Viscous yellow liquid | Yellow waxy solid | Viscous liquid | Emulsion | Emulsion |
| 2.25 | 4 | Viscous yellow liquid | Yellow waxy solid | Viscous liquid | Emulsion | Emulsion |
| 2.5 | 4 | Viscous yellow liquid | Yellow waxy solid | Viscous liquid | Yellow solution | Yellow color solution |
| 2.75 | 4 | Viscous yellow liquid | Pale yellow waxy solid | Viscous liquid | Pale yellow solution | Very pale yellow color solution |
| 3.0 | 4 | Viscous yellow liquid | Pale yellow solid | Viscous liquid (half solid half viscous liquid) | Clear solution | Clear solution |
| 4.0 | 4 | Viscous yellow liquid | Pale yellow waxy solid | Pale yellow waxy solid | Clear solution | Clear solution |

Conclusions.

These studies show that the polymer HCO-60 can be used to entrap compound 1001 with Hot Melt method. HCO-40 did not develop waxy solid at higher weight percent (3.0%) under the conditions of this study. On the otherhand, HCO-60 developed waxy solid at 2.0 wt %. This method has unique advantages of being an easy and fast method that avoids the use of organic solvent in the preparation of MNF. Also, the method of preparation is easy and fast. The waxy solid developed in stage 1 may be helpful in preventing the drug degradation and help the drug to stay in waxy solid state at room temperatures with a blanket of inert gas. Qualitative proton NMR studies show that drug is not freely available when resuspended in aqueous solution. On the otherhand, when the same formulation was resuspended in organic solvent, $CDCl_3$, drug peaks were clearly evident indicating the presence of drug in the outer organic solvent environment due to the formation.

Example 5

Preparation of Mixed Nanomicellar Cyclosporine Formulation

MNF formulation of cyclosporineA (Cys-A) was prepared by solvent evaporation method in two steps: 1. Preparation of basic formulation and 2. rehydration. In step one, cyclosporine, HCO-40 and octoxynol-40 were dissolved separately in 0.5 mL of ethanol aliquots. These three solutions were mixed together in a round bottom flask. The resultant mixture was stirred to obtain a homogenous solution. Ethanol solvent was removed by high speed vacuum evaporation overnight to obtain a solid thin film. In step two, the resultant thin film was hydrated with 2.0 mL of double distilled deionized water and resuspended with stirring overnight. The rehydrated formulation was pH adjusted and volume was made up with 2× phosphate buffer solution, (pH 6.8). Further the formulation was filtered through 0.2 μm nylon filter membrane to remove the unentrapped drug aggregates and other foreign particulates.

Different polymer weight percent combination than were used for the above resolvin examples were used to develop aqueous MNF entrapping 0.2 wt % cyclosporine-A. Formulations were characterized for their appearance, size and polydispersity indices. The formulations were found to be clear and have very small size with narrow polydispersity index. The results are summarized in tables 3a and 3b.

TABLE 3a

Cyclosporine mixed nanomicellar formulations at lower polymer concentrations.

| HCO-40 wt % | Octoxynol-40 wt % | Visual appearance | Size (nm) | Polydispersity index |
|---|---|---|---|---|
| 0.5 | 0.1 | Emulsion | N.D | N.D |
| 0.75 | 0.1 | Emulsion | N.D | N.D |
| 1 | 0.1 | Emulsion | N.D | N.D |
| 1.25 | 0.1 | Emulsion | N.D | N.D |
| 1.5 | 0.1 | Emulsion | N.D | N.D |
| 1.75 | 0.1 | Clear solution | 14.86 | 0.062 |
| 2.00 | 0.1 | Clear solution | 36.14 | 0.884 |
| 0.5 | 0.5 | Emulsion | N.D | N.D |
| 0.75 | 0.5 | Emulsion | N.D | N.D |
| 1 | 0.5 | Emulsion | N.D | N.D |
| 1.25 | 0.5 | Emulsion | N.D | N.D |
| 1.5 | 0.5 | Emulsion | N.D | N.D |
| 1.75 | 0.5 | Clear solution | 14.81 | 0.075 |
| 2.00 | 0.5 | Clear solution | 21.27 | 0.295 |

TABLE 3a-continued

Cyclosporine mixed nanomicellar formulations at lower polymer concentrations.

| HCO-40 wt % | Octoxynol-40 wt % | Visual appearance | Size (nm) | Polydispersity index |
|---|---|---|---|---|

N.D—Not Determined.

TABLE 3b

Cyclosporine mixed nanomicellar formulations at higher polymer concentrations.

| HCO-40 wt % | Octoxynol-40 wt % | Visual appearance | Size (nm) | Polydispersity index |
|---|---|---|---|---|
| 0.5 | 1.0025 | Clear solution | 12.9 | 0.069 |
| 0.5 | 2 | Clear solution | 18.1 | 0.069 |
| 2.5 | 0.005 | Clear solution | 15.65 | 0.064 |
| 2.5 | 1.0025 | Clear solution | 14.56 | 0.096 |
| 2.5 | 1.0025 | Clear solution | 14.81 | 0.078 |
| 2.5 | 1.0025 | Clear solution | 14.80 | 0.098 |
| 2.5 | 1.0025 | Clear solution | 14.45 | 0.102 |
| 2.5 | 2 | Clear solution | 13.92 | 0.108 |
| 4.5 | 0.005 | Clear solution | 20.59 | 0.271 |
| 4.5 | 1.0025 | Clear solution | 15.08 | 0.087 |
| 4.5 | 2 | Clear solution | 15.37 | 0.079 |

Water Method.

MNF formulation of cyclosporinA (CsA) was prepared by the water method. One mL of double distilled deionized water was heated to 60° C. in a round bottom flask. This heated water was kept under stirring. HCO-40 was added to the heated water and allowed to dissolve under constant stirring. Octoxynol-40 was then added to this mixture and allowed to dissolve. In a separate container, phosphates, sodium chloride and CsA were blended by hand shaking for a few minutes. Under stirring conditions, the phosphates/CsA/sodium chloride blend was added to the solution of HCO-40 and octoxynol-40 to disperse the drug. This mixture was allowed to cool to room temperature while stirring and check for complete dissolution of drug. PVP K 90 solution was separately prepared using the remaining 1 mL double distilled deionized water. This PVP K 90 solution was added to the solution of polymer/surfactant/drug/phosphate/sodium chloride. Water was added to make up the final volume. Then the formulation was filtered through 0.2 μm nylon membrane to remove the drug aggregates and other foreign particulates.

Example 6

Local Tolerability in Rabbits of Formulations

Healthy young adult New Zealand albino rabbits (3-4 Kg) used for the study the local tolerability of the instant formulations, for example a formulation of Examples 1-5. One drop (approximately 30 .mu.L) of saline is placed in one eye and a drop of formulation is placed in the other eye of the rabbit. Both eyes of each animal are examined by a veterinary ophthalmologist using a hand-held slit lamp and indirect ophthalmoscope. Both control and test eyes are graded according to conjunctival congestion, swelling, and discharge, aqueous flare, iris light reflex and involvement, corneal cloudiness severity and area, pannus, fluorescein examination and lens opacity using the Hackett/McDonald scoring system (see, for example, Hackett, R. B. and McDonald, T. O. Ophthalmic Toxicology and Assessing Ocular Irritation. Dermatoxicology, 5 .sup.th Edition. Ed. F. N. Marzulli and H. I. Maibach. Washington, D.C.: Hemisphere Publishing Corporation. 1996; 299-305 and 557-566.). In the fluorescein examination, approximately one drop of 0.9% sodium chloride, USP, is applied to the end of a fluorescein impregnated strip and then applied to the superior sclera of the left and right eyes (one fluorescein impregnated strip is used for each animal). After an approximate 15 second exposure, the fluorescein dye is gently rinsed from each eye with 0.9% sodium chloride, USP. The eyes are then examined using a slit lamp with a cobalt blue filtered light source. For the lenticular examination approximately one drop of a short-acting mydriatic solution is instilled onto each eye in order to dilate the pupil. After acceptable dilation has occurred, the lens of each eye is examined using a slit-lamp biomicroscope.

The crystalline lens is observed with the aid of the slit-lamp biomicroscope, and the location of lenticular opacity is discerned by direct and retro illumination. The location of lenticular opacities are arbitrarily divided into the following lenticular regions beginning with the anterior capsule: Anterior subcapsular, Anterior cortical Nuclear Posterior cortical, Posterior subcapsular, Posterior capsular. The lens is evaluated routinely during ocular evaluations and graded as either 0 (normal) or 1 (abnormal). The presence of lenticular opacities are described and the location noted.

Example 7

Ocular Tissue Distribution of Formulations of 0.05 wt %, 0.2 wt % and 0.5 wt % in Mixed Micellar Formulations of the Present Disclosure The temporal distribution and potential accumulation with repeat dosing, gender difference, and potential melanin binding of (ophthalmic solution) of the present disclosure (for example the formulations of Examples 1-5) after ocular application is assessed by determining concentration of active ingredients in ocular tissues, tears, and blood in New Zealand White (NZW) and Dutch Belted (DB) rabbits.

NZW rabbits are used in a single dose (SD) and 7-day repeat dose (RD) studies. DB rabbits will be used in a single dose study). Animals are either untreated (controls) or given a single or a daily topical ocular dose for 7 days (0.05 wt %, 0.2 wt % or 0.5 wt % in a mixed micellar formulation to one or both eyes). Blood and ocular tissue concentrations are assessed.

The concentration of drug is in tissues in the front of the eye (cornea, conjunctiva, sclera) and at the back of the eye (retina, optic nerve) but minimal in the middle of the eye (aqueous and vitreous humor), suggesting transport of the drug by a mechanism other than passive transport through the eye. The high drug levels achieved at the back of the eye make topical administration of the compositions of the present disclosure feasible for the treatment of diseases of the back-of-the-eye (e.g., retinal, diseases involving optic nerve such as glaucoma). Very high levels, especially in target tissues such as lachrymal gland, will be shown with the compositions of the present disclosure.

Example 8

Use of Resolvin Mixed Nanomicellar Formulations for Treating Dry Eye

Mixed nanomicellar formulations according to Examples 1-5 are administered to an patient having dry eye at a concentration of between 0.05% and 0.2% b.i.d. over a period of 1 month to 1 year or more.

Example 9

Use of Resolvin Mixed Nanomicellar Formulations for Treating Diabetic Retinopathy Mixed nanomicellar formulations according to Examples 1-5 are administered to an patient having proliferative diabetic retinopathy at a concentration of between 0.2 wt % to 0.5 wt % b.i.d. over a period of 1 month to 1 year or more.

Example 10

Tolerance and Ocular Tissue Distribution of Cyclosporine Mixed Nanomicellar Formulations A study was conducted in rabbits to test the tolerance and ocular tissue distribution of a nanomicellar formulation of cyclosporine against its placebo and balanced saline solution (BSS). Healthy New Zealand female white rabbits (2-3 kg) were used for this study. Cyclosporine study drug was prepared having 0.1% cyclosporine essentially as described in the examples herein. The below table shows the formulation composition of the CsA formulation and the Placebo.

TABLE 4

Formulation Composition:

| Components | CsA 0.1% formulation | Placebo |
|---|---|---|
| Cyclosporine | 0.1% | 0 |
| Hydrogenated castor oil-40 | 1.0% | 1.0% |
| Octoxynol-40 | 0.05% | 0.05% |
| Sodium chloride | 0.10% | 0.10% |
| PVP-K90 | 0.60% | 0.60% |
| Disodium EDTA | 0.05% | 0.05% |
| Benzalkonium chloride | 0.003% | 0.003% |
| Sodium Phosphate buffer | ~0.4% | ~0.4% |
| pH | 7 | 7 |

One drop (approximately 35 µL) of study drug was applied o.d. 4×/day at two hour intervals for 5 days. One drop of BSS was applied to the contralateral eye.

The tolerance parameters evaluated were: physical examination (acclimation study release); viability (daily); clinical observations (daily); Hackett-McDonald Ocular Irritation scores (pre-dose baseline data for each rabbit and then a pre-dose [prior to first daily dose] each day and then 30 min after last dose daily, intraocular pressure (IOP) pre-dose baseline data for each rabbit and then 30 minutes after the evening examinations each day, electroretinography (ERG) pre-dose-(pre-study) baseline data for each rabbit and then one hour after the last treatment, and ocular histopathology at euthanasia.

Mean cumulative Hackett-McDonald ocular irritation scores demonstrated very minimal scores for both BSS-treated left eyes and cyclosporine treated right eyes throughout the study, both for pre-treatment and post-treatment examination times. Mean cumulative inflammatory scores of less than 2 were observed in eyes treated with the TA, placebo, and BSS. These clinical scores represented mild conjunctival hyperemia (redness) and swelling. However, there were no significant differences in mean cumulative Hackett-McDonald ocular irritation scores between the groups, suggesting no difference in irritation from topical application of 0.1% CsA in HCO-40, the HCO-40 placebo, and BSS.

No changes in IOP were noted in eyes treated with BSS, HCO-40, or CsA. No toxicologic changes in retinal function were noted on ERG after 5 days of treatment with the test articles. No toxicologic or inflammatory changes were observed histologically in the anterior (conjunctiva/cornea/iris) or posterior segments (vitreous/retina) of the eye of any groups.

Samples of selected ocular tissues (aqueous humor, vitreous humor, conjunctiva, cornea, iris-ciliary body, lens, retina/choroid, and sclera) were collected 1 hour following the last dose on Day 5 from all two rabbits that received 0.1% CsA with HCO-40 (OD), and BSS (OS), and from one rabbit (No. 21) that received placebo HCO-40 formulation (OD) and BSS (OS). The samples were assayed for cyclosporine (CsA) by liquid chromatography-tandem mass spectrometry (LC-MS/MS). The internal standard was $d_4$-cyclosporine. The established analytical ranges for CsA were 0.100-100 ng/mL for whole blood, and 2.00-2000 ng/mL for aqueous humor and vitreous humor. The analytical ranges for the solid tissues were 0.125-30 ng (low range) and 1.00-2500 ng (high range). The results of the solid tissue analyses were converted to ng/g by correcting for the amount of tissue analyzed.

Concentrations of CsA in ocular tissues collected 1 hour following the last dose on Day-5 are summarized in Table 5. Following repeated administration of the 0.1% CsA HCO-40 formulation, the highest average CsA concentrations in the treated eye were observed in cornea (7805 ng/g), followed by conjunctiva (2125 ng/g), sclera (720 ng/g), iris-ciliary body (204 ng/g), and aqueous humor (134 ng/mL). The lowest CsA concentrations were observed in the lens (68.6 ng/g), retina/choroid (54 ng/g), and vitreous humor (~8 ng/mL). CsA concentrations in the collateral eye treated with BSS were quite low suggesting minimal systemic transfer of drug.

The ocular tissue concentrations for the 0.1% CsA formulation observed in this study were generally higher than the $C_{max}$ values following repeat dose administration (bid for 7 days) of an Allergan 0.2% 3H cyclosporine A formulation to rabbits (see Acheampong A A, Shackleton M, Tang-Liu D, Ding S, Stern M E, Decker R Distribution of cyclosporin A in ocular tissues after topical administration to albino rabbits and beagle dogs; Current Eye Research 18(2); 1999; pp 91-103).

TABLE 5

| Matrix | Nanomicellar 0.1% CsA | Allergan 0.2% CsA |
|---|---|---|
| Aqueous Humor | 134.5 ng/mL | 19.3 ng-eq/mL |
| Vitreous Humor | 8.37 ng/mL | 0.810 ng-eq/mL |
| Sclera | 720.5 ng/g | 35.2 ng-eq/g |
| Conjunctiva | 2125 ng/g | ND ng-eq/g |
| Cornea | 7805 ng/g | 6011 ng-eq/g |
| Iris-Ciliary Body | 204 ng/g | 109 ng-eq/g |
| Lens | 68.6 ng/g | 39.6 ng-eq/g |
| Retina/Choroid | 53.7 ng/g | 4.62 ng-eq/g |

Example 11

Tolerance and Ocular Tissue Distribution of Compound 1001 Mixed Nanomicellar Formulations A study was conducted in rabbits to test the tolerance and ocular tissue distribution of two nanomicellar formulations of compound 1001 (RX10045) against matching placebos (Table 6a and 6b) and balanced saline solution (BSS). Healthy New Zealand female white rabbits (2-3 kg) were used for this study. One drop (approximately 35 µL) of study drug was applied o.d. 4×/day at two hour intervals for 5 days. One drop of BSS was applied to the contralateral eye.

The tolerance parameters evaluated were: physical examination (acclimation study release); viability (daily); clinical observations (daily); Hackett-McDonald Ocular Irritation scores (pre-dose baseline data for each rabbit and then a pre-dose [prior to first daily dose] each day and then 30 min after last dose daily, intraocular pressure (IOP) pre-dose baseline data for each rabbit and then 30 minutes after the evening examinations each day, electroretinography (ERG) pre-dose-(pre-study) baseline data for each rabbit and then one hour after the last treatment, and ocular histopathology at euthanasia.

TABLE 6a

Formulation Composition: RX-10045 0.15%

| Components | RX-10045 (0.1%) in HCO-40 percentage | Placebo percentage |
|---|---|---|
| RX-10045 | 0.1% | 0 |
| Hydrogenated Castor Oil-40 | 1.0% | 1.0% |
| Octoxynol-40 | 0.05% | 0.05% |
| Sodium chloride | 0.10% | 0.10% |
| PVP-K90 | 0.60% | 0.60% |
| Disodium EDTA | 0.05% | 0.05% |
| Benzalkonium chloride | 0.003% | 0.003% |
| Sodium Phosphate buffer | ~0.4% | ~0.4% |
| pH | 5.5 | 5.5 |

TABLE 6b

Formulation Composition: RX-10045 0.1%

| Components | RX-10045 (0.15%) in HCO-60 percentage | Placebo Percentage |
|---|---|---|
| RX-10045 | 0.15% | 0 |
| Hydrogenated Castor Oil-60 | 1.0% | 1.0% |
| Octoxynol-40 | 0.05% | 0.05% |
| Sodium chloride | 0.10% | 0.10% |
| PVP-K90 | 0.60% | 0.60% |
| Disodium EDTA | 0.05% | 0.05% |
| Benzalkonium chloride | 0.003% | 0.003% |
| Sodium Phosphate buffer | ~0.4% | ~0.4% |
| pH | 5.5 | 5.5 |

Cumulative Hackett-McDonald ocular irritation scores demonstrated very minimal mean values for both BSS-treated left eyes and test-article treated right eyes throughout the study, both for pre-treatment and post-treatment examination times. There were no significant differences in mean cumulative Hackett-McDonald ocular irritation scores between the groups (Table 7). The observed ocular irritation was interpreted as minimal and transient in all groups.

TABLE 7

Hackett-McDonald Composite Scores (mean ± s.d.)

| | JICO-40 Placebo[a] | RX-10045 0.1%[b] | JICO-60 Placebo[a] | RX-10045 0.15%[b] |
|---|---|---|---|---|
| Day 1 Predose | 0.0-0.0 | 0.0-0.0 | 0.0-0.0 | 0.0-0.0 |
| Day 1 Postdose | 1.7-1.5 | 0.5-0.1 | 0.0-0.0 | 0.5-0.1 |
| Day 2 Predose | 0.0-0.0 | 0.0-0.0 | 0.0-0.0 | 1.0-1.2 |
| Day 2 Postdose | 2.0-0.0 | 0.0-0.0 | 07.-1.1 | 0.5-1.0 |
| Day 3 Predose | 0.0-0.0 | 0.0-0.0 | 0.0-0.0 | 0.5-1.0 |
| Day 3 Postdose | 1.3-1.2 | 0.0-0.0 | 0.0-0.0 | 1.0-1.2 |
| Day 4 Predose | 1.3-1.2 | 0.0-0.0 | 0.3-0.6 | 0.5-1.0 |
| Day 4 Postdose | 1.3-1.2 | 0.0-0.0 | 0.7-1.2 | 0.8-1.0 |
| Day 5 Predose | 0.0-0.0 | 0.5-1.0 | 1.0-1.0 | 0.0-0.0 |
| Day 5 Postdose | 1.3-2.3 | 0.0-0.0 | 0.3-0.6 | 0.8-1.1 |

No changes in TOP were noted in eyes treated with BSS or test articles. No toxicologic changes in retinal function were noted on ERG after 5 days of treatment with the test articles. No toxicologic or inflammatory changes were observed histologically in the anterior (conjunctiva/cornea/iris) or posterior segments (vitreous/retina) of the eye of any groups.

Selected ocular fluids/tissues (aqueous humor, vitreous humor, conjunctiva, cornea, iris-ciliary body, lens, retina/choroid, and sclera) collected from two rabbits each in the RX-10045 (0.15% in HCO-60, 0.1% in HCO-40) treatment groups, and from one rabbit in each of the matching placebo groups, were assayed for compound 1001 and another resolvin by liquid chromatography-tandem mass spectrometry (LC-MS/MS). Warfarin-$d_5$ and 5-HDA were used as internal standards for the analysis of RX-10045 and its active metabolite, RX-10008, respectively, in aqueous humor and vitreous humor. For the other ocular tissues (solid tissues), warfarin-d5 and phenyl acetic acid-d5 (PAA-$d_5$) were used as the internal standards for compound 1001 and RX-10008, respectively. The analytical range for the solid tissues were 0.125-100 ng. The results of the solid tissue analyses were converted to ng/g by correcting for the amount of tissue analyzed.

Only sporadic, relatively low, concentrations of the compound 1001 ester prodrug were observed in the sclera and conjunctiva. Compound 1001 was either not detected or was below the quantitation limit of the assay in the majority of ocular tissues. These data suggest that RX-10045 was rapidly hydrolyzed to its active metabolite, RX-10008.

A summary of the parent compound (RX-10008) tissue concentrations are presented in Table 8. The highest concentrations of RX-10008 were found in the cornea, followed by the iris-ciliary body, conjunctiva, and sclera. There were also relatively high concentrations of RX-10008 in the aqueous humor. Lower amounts were found in the retina/choroid and lens. The lowest levels of RX-10008 were found in the vitreous humor.

TABLE 8

Comparison of mean (n = 2) RX-10008 ocular tissue concentrations following topical ocular administration of RX-10045 (0.15% in HCO-60, 0.1% in HCO-40) formulations to the eye four times a day at 2 hour intervals for five days to New Zealand White Rabbits

| | Treatment Group 4 0.15% RX-10045 in HCO-60 | Treatment Group 5 0.1% RX-10045 in HCO-40 |
|---|---|---|
| | RX-1008 (ng/g or ng/mL) | |
| Sclera | 990[a] | 701 |
| Cornea | 15700[a] | 9650[a] |
| Conjunctiva | 1132 | 879 |
| Lens | 136 | 164 |

TABLE 8-continued

Comparison of mean (n = 2) RX-10008 ocular tissue concentrations following topical ocular administration of RX-10045 (0.15% in HCO-60, 0.1% in HCO-40) formulations to the eye four times a day at 2 hour intervals for five days to New Zealand White Rabbits

|  | Treatment Group 4 0.15% RX-10045 in HCO-60 | Treatment Group 5 0.1% RX-10045 in HCO-40 |
|---|---|---|
|  | RX-1008 (ng/g or ng/mL) | |
| Iris-Ciliary Body | 2725 | 2655 |
| Retina/Choroid | 410 | 323 |
| Vitreous Humor | 18 | 15.7 |
| Aqueous Humor | >2000 | >2000 |

$^a$n = 1

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. An aqueous clear nanomicellar ophthalmic formulation comprising 0.05-0.5% by weight cyclosporine, a polyalkoxylated alcohol and one or more polymers comprising HCO-40, HCO-60, HCO-80, HCO-100, polyoxyl 35 castor oil or combinations thereof.

2. The aqueous clear nanomicellar ophthalmic formulation of claim 1, wherein said polymer comprises HCO-40, HCO-60, HCO-80, HCO-100 or combinations thereof.

3. The aqueous clear nanomicellar ophthalmic formulation of claim 1, wherein said polymer comprises polyoxyl 35 castor oil.

4. The aqueous clear nanomicellar ophthalmic formulation of claim 1, wherein said polymer is HCO-40.

5. The aqueous clear nanomicellar ophthalmic formulation of claim 1, wherein said polymer is 0.5-1.5% by weight of the formulation.

6. The aqueous clear nanomicellar ophthalmic formulation of claim 1, wherein said polymer comprises HCO-40 HCO-60, HCO-80, or combinations thereof and is 0.5-1.5% by weight of the formulation.

7. The aqueous clear nanomicellar ophthalmic formulation of claim 1, wherein said polyalkoxylated alcohol comprises Octoxynol-40.

8. The aqueous clear nanomicellar ophthalmic formulation of claim 1, wherein the polyalkoxylated alcohol comprises Octoxynol-40 and is 0.02-4% by weight of the formulation.

9. The aqueous clear nanomicellar ophthalmic formulation of claim 1, wherein the polyalkoxylated alcohol comprises Octoxynol-40 and is 0.02-0.1% by weight of the formulation.

10. The aqueous clear nanomicellar ophthalmic formulation of claim 1, wherein the cyclosporine is 0.05-0.2% by weight of the formulation.

11. The aqueous clear nanomicellar ophthalmic formulation of claim 1, wherein said polymer comprises HCO-40, HCO-60, HCO-80, HCO-100 or combinations thereof; and wherein said polyalkoxylated alcohol is Octoxynol-40.

12. The aqueous clear nanomicellar ophthalmic formulation of claim 1, wherein said polymer is 0.5-1.5% by weight of the formulation; and said polyalkoxylated alcohol is Octoxynol-40 and is 0.02-0.1% of the formulation.

13. The aqueous clear nanomicellar ophthalmic formulation of claim 1, wherein said polymer is 0.5-1.5% of the formulation; said polyalkoxylated alcohol comprises Octoxynol-40 and is 0.02-0.1% of the formulation; and the cyclosporine is 0.05-0.2% of the formulation.

14. A method of treating or preventing an ocular disease or condition, said method comprising topically administering an aqueous clear nanomicellar formulation of claim 1.

15. A method of treating or preventing an ocular disease or condition, said method comprising topically administering an aqueous clear nanomicellar formulation of claim 13.

16. The aqueous clear nanomicellar ophthalmic formulation of claim 1, wherein said formulation provides higher average concentration of cyclosporine in cornea, conjunctiva and sclera in comparison to higher marketed strength.

17. The aqueous clear nanomicellar ophthalmic formulation of claim 1, wherein said formulation demonstrates mean cumulative inflammatory score of less than 2.

\* \* \* \* \*